United States Patent [19]

Kawahara et al.

[11] Patent Number: 4,738,622
[45] Date of Patent: Apr. 19, 1988

[54] REMOVABLE DENTURE RETAINING STRUCTURE

[75] Inventors: Haruyuki Kawahara, 28 Tokyo-cho, 1-chome, Moriguchi-shi, Osaka-fu; Hiroki Wada, Osaka; Takashi Tsutsumi, Hyogo; Ikuya Matsuo, Ibaragi, all of Japan

[73] Assignees: Wada Seimitsu Shiken Kabushiki Kaisha, Osaka; Nippon Maktron Kabushiki Kaish, Tokyo; Haruyuki Kawahara, Osaka, all of Japan

[21] Appl. No.: 890,810

[22] Filed: Jul. 24, 1986

Related U.S. Application Data

[63] Continuation of Ser. No. 652,314, Sep. 19, 1984, abandoned.

[30] Foreign Application Priority Data

Oct. 7, 1983 [JP] Japan ................................. 58-189050

[51] Int. Cl.⁴ ............................................. A61C 13/28
[52] U.S. Cl. .................................... 433/169; 433/173; 433/180
[58] Field of Search ............... 433/180, 167, 168, 169, 433/181, 173, 177

[56] References Cited

U.S. PATENT DOCUMENTS

| 2,036,678 | 4/1936 | Blake | 433/168 |
| 3,934,347 | 1/1976 | Lash | 433/180 |
| 3,958,334 | 5/1976 | Heimansohn | 433/169 |
| 4,014,095 | 3/1977 | Heimansohn | 433/169 |
| 4,204,321 | 5/1980 | Scott | 433/177 |
| 4,215,986 | 8/1980 | Riess | 433/169 |
| 4,318,696 | 3/1982 | Kasama | 433/169 |
| 4,324,549 | 4/1982 | Madray | 433/169 |

Primary Examiner—John J. Wilson
Attorney, Agent, or Firm—Koda and Androlia

[57] ABSTRACT

The specification discloses a removable denture retaining structure in which an elastic mounting member is provided between a denture body and a support base. This structure can obviate all problems of the prior art, i.e. many parts are required, skilled technique is also required to produce, mount and dismount the denture body, and looseness and breakage due to fatigue are apt to occur. Furthermore, the invention is advantageous because the structure can provide patients with comfortable feeling during use.

14 Claims, 4 Drawing Sheets

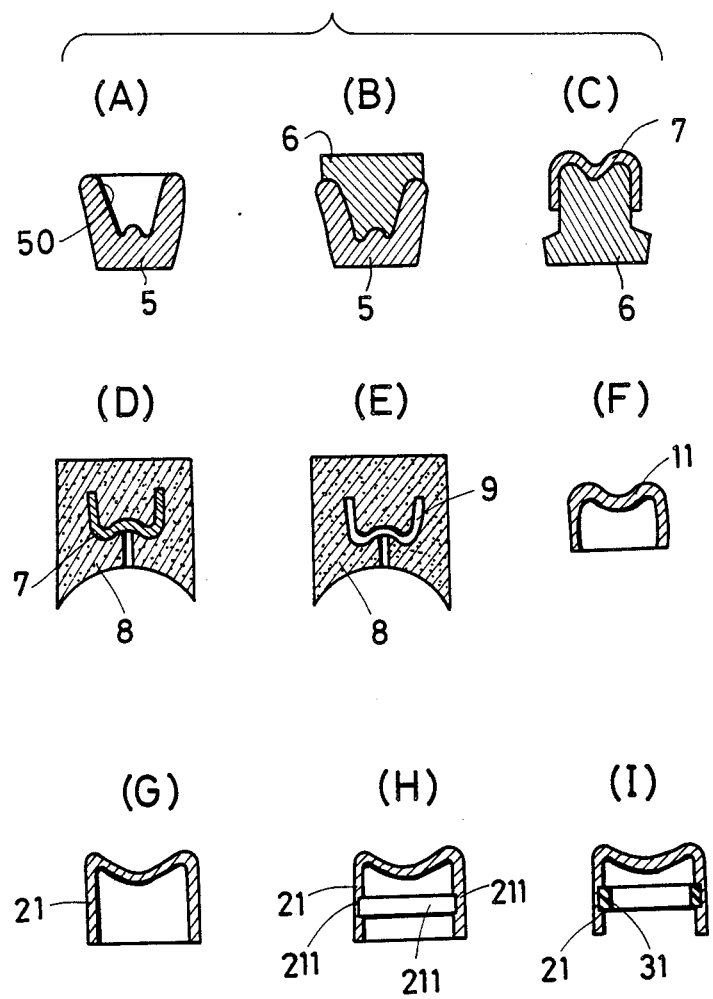

REMOVABLE DENTURE RETAINING STRUCTURE

This is a continuation of application Ser. No. 652,314, filed Sept. 19, 1984, now abandoned.

BACKGROUND OF THE INVENTION

1. Field of the Invention

This invention relates generally to improvements in denture retaining structures and more particularly to improvements in removable retaining structures composed of support bases and denture bodies for removable dentures, removable crown and bridge (hereafter both are simply referred to as dentures).

2. Prior Art

Known retaining structures which retain such dentures on jaws so that they are removable when required for cleaning or repair are mainly metallic retaining structures. One structure for example uses a screw or another fixture to connect an support base with a denture body. Another structure uses a metallic inner crown placed over a natural remaining tooth and capped by a metallic outer crown secured in a denture body to provide a telescopic structure.

The former structure, however, uses many parts and requires skills because mounting and removal are troublesome. The latter structure is apt to generate looseness and breakage due to wear caused by fatigue. It also needs complicated and advanced technology.

SUMMARY OF THE INVENTION

It is therefore an object of the present invention to solve these problems. With this invention, an elastic mounting member made of polyurethane rubber, segment polyurethane rubber or composite materials of these rubber materials is formed as desired and placed between a support base and a denture. In the secured condition, a friction force caused by elastic compression and/or mechanical engagement of the elastic mounting member prevents the denture from sinking in or floating from the support base during normal biting motion. When an external force different from the biting force is applied and the denture body is strongly lifted, the member is elastically compressed and deformed, so that the denture body can be removed upward from the support base. Since the member has good moldability, it can be molded in any forms and dimensions matching all tooth conditions. In addition, the member is superior in elasticity, wear resistance and durability. As a result, the construction, fabrication and handling of the structure are significantly simplified. Preferred embodiments of this invention are shown in connection with the drawings.

DETAILED DESCRIPTION OF THE PREFERRED EMBODIMENTS

Figure 1:
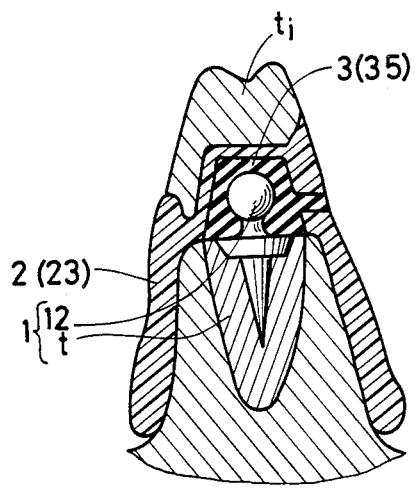
FIG. 1 is a longitudinal sectional view of the first embodiment of the present invention.

A removable denture retaining structure which is commonly adapted for the first to ninth embodiments of the present invention includes an support base (1) and a denture body (2) which is removably secured on the support base (1). The denture body (2) is integrated with an elastic mounting member (3) which is made of polyurethane rubber, segment polyurethane rubber or composite materials of these rubber materials and is formed as desired. The elastic mounting member (3) is mounted between the support base (1) and the denture body (2) to prevent the denture body from sinking in or floating from the support base (1) during normal biting motion. When an external force different from the biting force is applied and strongly lifted, the elastic mounting member (3) is elastically compressed and deformed so that the denture body can be removed from the support base. The polyurethane rubber used in the present invention is made so that it has enough elasticity to provide a sufficient friction force when compressed, to prevent the denture body from sinking in or floating from the support base during normal biting motion. The polyurethane rubber has also such elasticity characteristics as to allow the denture body to be easily removed from the support base when an external force coping with the friction is applied to the rubber by a dentist. The polyurethane rubber has a modulus of elasticity of 10 to 1,000 kg/cm$^2$, a coefficient of friction of 0.95 to 1.43 and a compression ratio of 0.46 to 0.50. The ranges of these physical properties can be further extended by copolymerization or composition as described later. In addition, the polyurethane rubber is stable for an extended period when it is exposed to food, saliva and soldes. The rubber is not easily discolored (yellowed) so that it is nice to look at for a long time. More specifically, polyether polyol, acrylic polyol, polybutadiene polyol or polycarbonate polyol is preferably selected as a main structure to reduce bonding (or hydrophile property due to bonding) of ester, allphanate, buret, etc. which is apt to be hydrolytically dissociated by weak acids (organic acids) or weak alkalis in a mouth. In addition, XDI (xylene diisocyanate), HDI (hexamethylene diisocyanate), HTDI (hydro TDI), HMDI (hydro MDI), IPDI (isophorone diisocyanate) or LDI (lysine diisocyanate) is preferably used as diisocyanate to reduce yellowing due to sunlight.

Two examples of polyurethane rubber materials with the above mentioned physical and chemical properties are described below.

(EXAMPLE 1)

About 30 to 50 parts of IPDI are added to and reacted with 100 parts of polycarbonate polyol (molecular weight:2,000,) at 100° C. for about 30 minutes, and then mixed with 30 to 50 parts of 3,3'-dichloro, 4,4'-diaminodiphenylmethane.

(EXAMPLE 2)

About 25 to 70 parts of HDI are added to and reacted with 100 parts of polybutadiene polyol (molecular weight:600), and then bridged by 3,3'-dichloro, 4,4'-diamino-diphenylmethane. These two are only examples.

The physical properties of the polyurethane rubber used for the present invention need to be changed according to the case in which the elastic mount member is used. In particular, the hardness, modulus of elasticity and coefficient of friction need to be changed. Chemically denatured rubber, physically composite rubber or intermediate materials of these rubber materials can be used to meet the needs. To increase the hardness, acrylate, ester maleate, methacrylate, styrene, epoxy, fluoro compound or silicon carbide is included in the side or main chain of polyurethane rubber to produce a copolymer, i.e., segment polyurethane rubber. Modulus of elasticity and coefficient of friction can be increased by physically blending polyurethane or the above-mentioned segment polyurethane rubber with PVC, chlorinated polyethylene, AS, ABS, cellulose propionate, silicone oil, polyether sulfone, bisphenol A epichlorohydrin resin or polytetramethylene-tetraphthalate, or by partially chemically bonding the exemplified polymer with polyurethane rubber or segment polyurethane rubber to produce a polymer blend. The product made by the former method is a physically composite material and the product made by the latter method is an intermediate material of chemical and physical composites. In the same way, polyurethane rubber or segment polyurethane rubber can also be composited with the following inorganic and organic substances. That is, polyurethane rubber or segment polyurethane rubber can be composited with organic fibers such as polyester fiber, polyamide fiber and aramid fiber, or ceramic fibers such as glass fiber, alumina fiber and carbon fiber, or metal fibers. Furthermore, polyurethane rubber or segment polyurethane rubber can be composited with powder of the organic fibers. Moreover, fabrics made of these fibers can be molded and integrated with the elastic mount member. The physical properties of these chemical and physical composited materials have the following wider ranges: a modulus of elasticity of 10 to 10,000 kg/cm$^2$, a coefficient of friction of 0.03 to 1.8 and a compression ratio of 0.32 to 0.50. The elastic mounting member of the present invention is made of the above-mentioned polyurethane rubber, segment polyurethane rubber or composited materials of these rubber materials. However, low-foamed substances made of these rubber materials including a small amount of foam can also be used according to the case. The low foamed substances have a better shock-absorbing function than solid substances.

If the foaming rate is too high, however, the desired elasticity may not be obtained. Therefore, foamed substances with a very high foaming rate should not be used.

In the case of another embodiment of the present invention, the elastic mounting member (3) is simply mechanically engaged with the support base (1) when the mounting member is mounted on the support base so that the denture body can be prevented from floating from or sinking in the support base.

When the elastic mounting member (3) is lifted with a great force, it is elastically compressed and deformed so that the denture body can be easily removed from the support base (1). In this case of the mechanical engagement, the friction force caused by elastic compression is not regarded important. This embodiment differs from the previously mentioned embodiment in this respect. However, to include both embodiments in the present invention, the above-mentioned rubber materials need to be applied.

Figure 2:
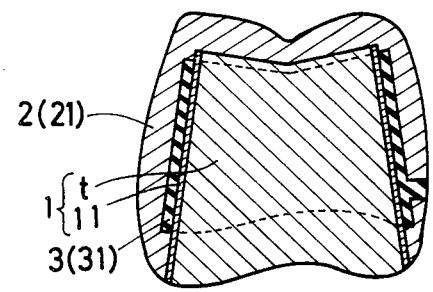
FIG. 2 is a longitudinal sectional view of the second embodiment of the present invention, FIGS. 3 (A) to 3(I) are production process drawings of the second embodiment of the present invention.

The embodiments of the present invention are classified as follows according to the performance of preventing denture body (2) from floating or sinking. The second embodiment corresponds to the former embodiment species (which uses the friction force caused by elastic compression), and the fourth and sixth embodiments correspond to the latter embodiment species (which uses mechanical engagement). Other embodiments (the first, third, fifth, seventh, eighth and ninth embodiments) correspond to both species. All embodiments will be considered in detail referring to the drawings. The first embodiment illustrates a denture of a lower jaw. As shown in FIG. 1, a natural abutment tooth base (t) and a metallic post (12) function as the support base (1). The denture body (2) is shown as a denture plate which is placed over the tooth (t). A metallic post (12) is embedded in the tooth (t), and a trapezoidal cap (35), which is placed over the post (12) and functions as the elastic mounting member (3), is integrated with the drown (denture plate) (23) made of synthetic resins (such as acrylic resin or polyurethane resin). (ti) refers to an artificial tooth. In this embodiment, the elastic mounting member (3), i.e. the trapezoidal cap (35) is placed over the post (12) so that the denture body (2) is removably connected with the tooth (t). More specifically, when an external force such as a biting force or a force to lift the tooth (ti) is applied to the connection (a lifting force is applied to the tooth (ti) when a sticky food such as rice cake is chewed and when the tooth (ti) separates from the mating natural tooth of an upper jaw), the connection is firmly maintained in the vertical direction by the friction force caused by elastic compression between the post (12) and the elastic mounting member (3). In addition, such external force is broken by the elastic deformation of the elastic mounting member (3). However, when a lifting force greater than the friction caused by elastic compression is applied to the tooth (ti) or the crown (23), the denture plate (2) can easily be removed from the tooth base (t). The second embodiment of FIG. 2 illustrates a removable crown. A metallic inner crown (11) and a natural tooth (t) function as the support base (1), and a metallic outer crown (21) functions as the denture body (2). A ring belt (31) inserted into the outer crown (21) functions as the elastic mounting member (3). (t) refers to a natural abutment tooth. When the outer crown (21) is placed over the inner crown (11), the ring belt (31) is compressed around its entire circumference in its thickness direction. A restoration force is generated and applied to the inner crown as the friction force caused by elastic compression.

This friction force prevents the outer crown (21) from sliding upward even when various external forces are applied to the outer crown (21). However, if an extraction force greater than the friction force caused by elastic compression is applied to the outer crown (21), the crown (21) can easily be removed. The thickness and shape of the ring belt (31) can be determined as desired. If the elastic mounting member (3) generates an excessive friction force, stripes (not shown) provided at appropriate intervals around the circumference can be used instead of the ring belt (31). The production process of the inner crown (11), outer crown (21) and ring belt (31) is explained referring to FIGS. 3 (A) to 3 (I).

First, a female model (5) with a cavity (50) which has the same shape as the contour of a remaining natural tooth (not shown) is formed using an impression material as shown in FIG. 3 (A). Next, the cavity (50) is filled with plaster slurry to produce a reversed male model (6) as shown in FIG. 3 (B). The male model (6) is placed upside down and a thin film of wax is coated on the male model (6) to obtain a wax model (7) which has the same shape as the contour of the natural tooth. Then, the wax model (7) is invested in a mold (8) as shown in FIG. 3 (D). The wax model (7) is heated and melted away to obtain a cavity (9) which has the same shape as the contour of the wax model as shown in FIG. 3 (E). Metal is casted in the cavity (9) to produce an inner crown (11) as shown in FIG. 3 (F). By using this inner crown (11) as a model, a metallic outer crown (21) is made as shown in FIG. 3 (G) in the same way as described above. A groove (211) is formed on the inner circumference of the outer crown (21) by machining as shown in FIG. 3 (H). Finally, polyurethane rubber or segment polyurethane rubber is poured into the groove (211) and cured to produce a ring belt (31) as shown in FIG. 3 (I). As described in this sequential process, the elastic mounting member (3) can be made by simply grooving the outer crown (21) and by pouring rubber in the groove and curing it, although the inner and outer crowns (11) and (21) are made using the conventional method. Since the ingredients of polyurethane rubber and segment polyurethane rubber have been adjusted to provide high flowability during low-temperature heating and at normal temperatures, an ordinary machine can be used. To obtain the elastic mounting member in which the above-mentioned fibers and powder are physically compounded with polyurethane robber or segment polyurethane rubber, the fibers and powder should be included in lost wax as required and prevented from flowing away when melted wax is melted awayso that they are integrated with cast polyurethane rubber or segment polyurethane rubber. In the embodiments described later, polyurethane rubber or segment polyurethane rubber is also exemplified as a material of the elastic mounting member for convenience. Instead of the ring belt (31) of the second embodiment, the third embodiment uses a notch (33) projected from the inner surface of the outer crown (21) as shown in FIG. 4.

The tip end of the notch (33) is elastically fit into a recess (111) on the outer side surface of the inner crown (11). It is obvious that the notch (33) in this embodiment functions as a substitute for the ring belt (3).

Figures 4, 5:
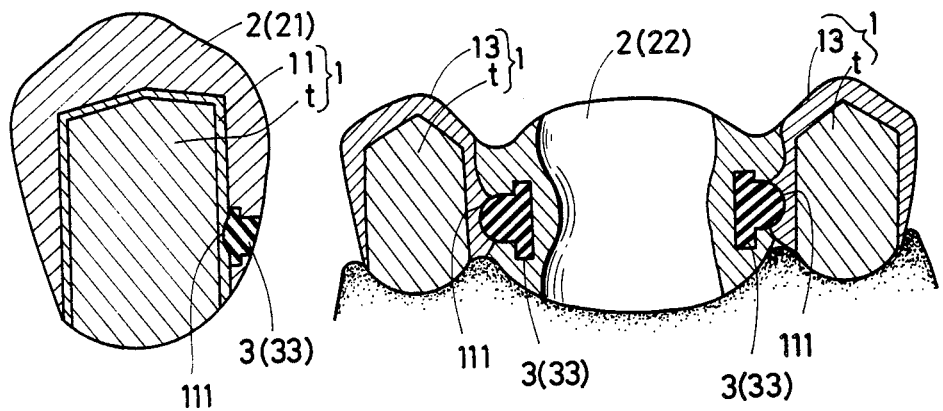
FIG. 4 is a longitudinal sectional view of the third embodiment of the present invention.
FIG. 5 is a longitudinal sectional view of the fourth embodiment of the present invention.

In the fourth embodiment, two natural abutment teeth (t), (t) and two bridge retainers (13), (13) function as the support base (1) and bridge (pontic) (22) functions as the denture body (2) as shown in FIG. 5. Two notches similar to the notch of the third embodiment and are made of polyurethane rubber of segment polyurethane rubber, are integrated with the bridge (22) and projected from the bridge. Each tip end of the notch (33) is mechanically engaged with the recess (111) on the outer side surface of each bridge retainer (13). In this embodiment, the bridge (22) is removable from the bridge retainers (13), (13). Elastic fitting of the notch (33) into the recess (111) applies unnecessary forces to natural tooth (t), (t) and is not desirable.

Figure 6:
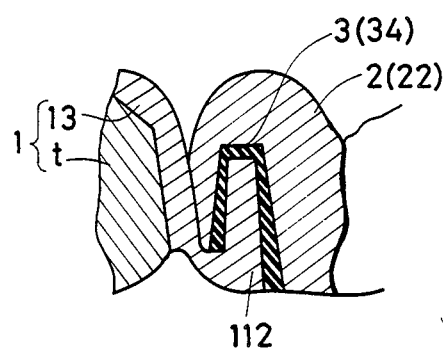
FIG. 6 is a longitudinal sectional view of the fifth embodiment of the present invention.

The fifth embodiment is a modification of the fourth embodiment. As shown in FIG. 6, two hat-shaped cap (34) provided in the bridge (22) function as the elastic mounting members (3). Each cap (34) is placed over a metallic post (112) projected from the outer surface of each bridge retainer (13) to form a removable bridge denture. Due to the deep fitting between the cap (34) and the post (112), this structure can cope with greater external biting forces than the structure of the fourth embodiment.

Figure 7:
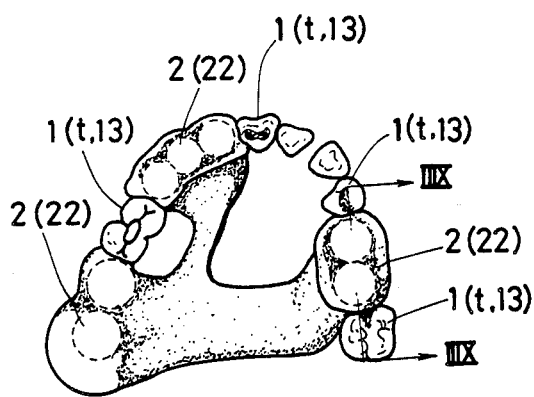
FIG. 7 is a top view of the six embodiment of the present invention.
Figure 8:
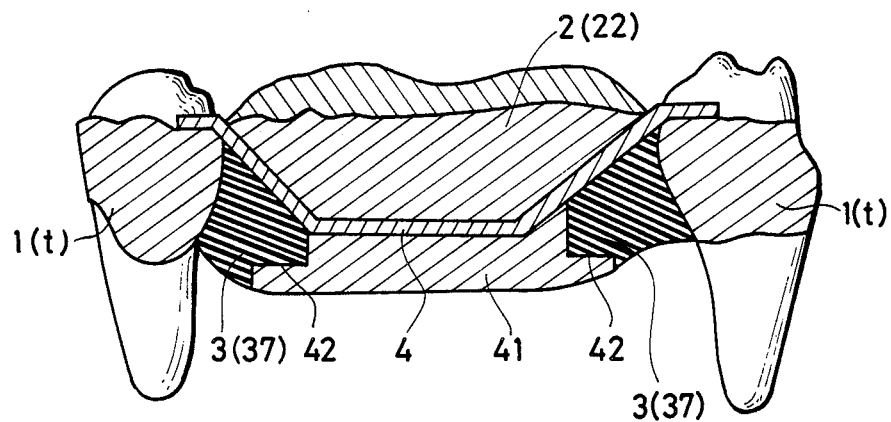
FIG. 8 is an enlarged sectional view taken on the planes of the lines IIX—IIX of FIG. 7.

The sixth embodiment illustrates a bridge denture of a lower jaw, which is a combination of a metallic rest (4) and the elastic mounting member (3) of the present invention. As shown in FIG. 8, which is an enlarged sectional view taken on the planes of the lines IIX—IIX of FIG. 7, the rest (4) is stretched between two natural abutment teeth (t), (t). The lower part of bridge (41) is provided under the rest (4), separated from the right and left the teeth (t), (t) via pockets (42), (42). Two elastic mounting members (3), (3) are included respectively in the pockets (42), (42) and mechanically engaged with the support bases (1) and function as wedges (37). Since the elastic friction forces of the wedges (37), (37) are applied to the sides of the teeth (t), (t), this structure can sufficiently cope with forces which lift the bridge (22). The rest (4) receives the compression force applied to the bridge (22) during biting motion.

Figure 9:
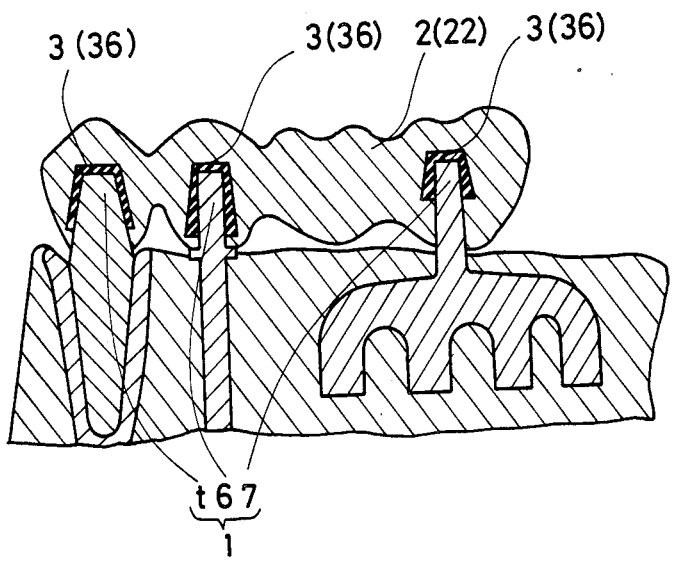
FIG. 9 is a longitudinal sectional view of the seventh embodiment of the present invention.
Figure 10:
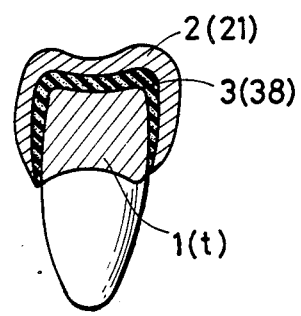

Elastic fitting of the wedges (37) into the pockets is not desirable because of the same reason as described for the fourth embodiment. The seventh embodiment illustrates a bridge denture over support bases composed of two kinds of implant members. As shown in FIG. 9, a natural abutment tooth (t), pin implant member (6) and blade implant member (7) function as the support bases (1), and the bridge (22) functions as the denture body (2). A hat-shaped caps (36), (36), (36), each made of polyurethane rubber or segment polyurethane rubber, are provided where the bridge (22) is placed over the support bases (t), (6) and (7). The bridge (22) is prevented from sinking in and floating from the support base (t), (6) and (7) using a capping structures similar to that of the fifth embodiment. FIG. 10 illustrates the eight embodiment. A cap (38) provided inside the metallic crown (21) functions as the elastic mounting member (3). The cap (38) is made of low-foamed polyurethane rubber or segment polyurethane rubber. The foamed material funcetion as a better shock absorber against external biting forces than a solid material.

Figure 11:
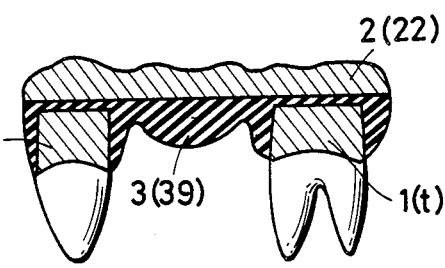
FIG. 10 is a longitudinal sectional view of the eighth embodiment of the present invention and FIG. 11 is a longitudinal sectional view of the ninth embodiment of the present invention.

FIG. 11 illustrates the ninth embodiment. A lower part of bridge (39), made of polyurethane rubber or segment polyurethane rubber, is located under the metallic bridge (22), is integrated with the bridge (22) and functions as the elastic mounting member (3). This structure of this embodiment provides better shock absorbing performance than the structure of the previously mentioned embodiment in which the elastic mounting member (3) is used as a part of the bridge (22).

With this invention, as clearly understood from the above-mentioned nine embodiments, the elastic mounting member made of polyurethane rubber, segment polyurethane rubber or composite materials of these rubber materials and is placed between the support base and the denture.

In the secured condition, the friction force caused by compression of the elastic mounting member and/or mechanical engagement of the elastic mounting member prevents the denture body from sinking in or floating from the support base during normal biting motion. This connection can be released by applying a strong lifting force Due to this simple structure, the present invention is advantageous because it can solve all problems of the prior art, i.e. many parts are required, skilled technique is also required to produce, mount and dismount the denture body, and looseness and breakage due to fatigue are apt to occur. Furthermore, unlike ready-made elastic members, the elastic mounting member of the present invention can be molded in any shapes and dimensions according to the case. Therefore, this structure can provide patients with comfortable feeling during use.

Having described our invention as related to the embodiments shown in the accompanying drawings, it is our intention that the invention be not limited by any of the details of description, unless otherwise specified, but rather be construed broadly within its spirit and scope as set out in the accompanying claims.

We claim:

1. A removable denture retaining structure including a support base and a denture body, said removable denture retaining structure being characterized in that said denture body is integrated with an elastic mounting member which is made from any of polyurethane rubber, segment polyurethane rubber and composite materials of these rubber materials and has at least the physical characteristics of the modulus of elasticity of 10 to 10,000 kg/cm$^2$, a coefficient of friction of 0.03 to 1.8 and a compression ratio of 0.32 to 050, and said elastic mounting member is removably pressure-fitted to said support base to elastically be in frictional contact therewith and to be in mechanical engagement therewith in an upward direction, so that said denture body does not float from or sink into said support base during normal biting motion, and so that said denture body can be removed from said support base when a great external force different from the biting force is applied to remove the denture body by compressing to deform said elastic mounting member.

2. A removable denture structure as claimed in claim 1, wherein said support base is a natural abutment tooth and a metallic post and said denture body is a crown placed over said support base.

3. A removable denture retaining structure as claimed in claim 2, wherein said elastic mounting member comprises said post set into said tooth and a trapezoidal cap which is placed over said post.

4. A removable denture retaining structure as claimed in claim 1, wherein said support base is a natural abutment tooth and an inner crown and said denture body is an outer crown.

5. A removable denture retaining structure as claimed in claim 4, wherein said elastic mounting member is a ring belt buried inside said outer crown.

6. A removable denture retaining structur as claimed in claim 4, wherein said elastic mounting member is a cap provided inside said outer crown.

7. A removable denture retaining structure as claimed in claim 6, wherein said cap is a low-foamed substance made of a material selected from the group consisting of polyurethane rubber, segment polyurethane rubber and composite materials of these rubber materials.

8. A removable denture retaining structure as claimed in claim 1, wherein a notch projected to the inner surface of said outer crown function as said elastic mounting member and the tip end of said notch is elastically fit in a recess provided on the outer side surface of said inner crown.

9. A removable denture retaining structure as claimed in claim 1, wherein said support base is two natural abutment teeth and two bridge retainers and said denture body is a bridge.

10. A removable denture retaining structure as claimed in claim 9, wherein two notches projected from said bridge function as said elastic mounting members and each tip end of said notch is mechanically engaged with a recess provided on the outer side surface of said bridge retainer.

11. A removable denture retaining structure as claimed in claim 9, wherein said elastic mounting member is two hat-shaped caps provided in said bridge, and each of said caps is placed over a post projected from the corresponding outer surface of each of said bridge retainer.

12. A removable denture retaining structure as claimed in claim 1, wherein a metallic rest of a bridge is stretched between and engages with two support bases, a lower part of said bridge is provided under said rest and separated from said support bases via pockets, and elastic mounting members of a wedge shape are provided in said pockets and mechanically engaged with said support bases.

13. A removable denture retaining structure as claimed in claim 1, wherein said support base is a natural abutment tooth and two implant members said denture body is a bridge, and said elastic mounting member is two hat-shaped caps provided in said bridge which are placed over said two implant members.

14. A removable denture retaining structure as claimed in claim 1, wherein said elastic mounting member is a lower part of said bridge.

* * * * *